United States Patent [19]

Hadley

[11] Patent Number: 4,480,099
[45] Date of Patent: Oct. 30, 1984

[54] DECAHYDROQUINOLYL BENZAMIDES

[75] Inventor: Michael S. Hadley, Sawbridgeworth, England

[73] Assignee: Beecham Group P.L.C., England

[21] Appl. No.: 390,353

[22] Filed: Jun. 21, 1982

[30] Foreign Application Priority Data

Jun. 22, 1981 [GB] United Kingdom ............... 8119186

[51] Int. Cl.³ .................. C07D 215/14; C07D 215/16
[52] U.S. Cl. .................................... 546/164; 424/258
[58] Field of Search ............................... 546/159, 164

[56] References Cited

U.S. PATENT DOCUMENTS 3,875,168 4/1975 Pfleiderer ........................... 546/164

FOREIGN PATENT DOCUMENTS 0013138 7/1980 European Pat. Off.
2417763 10/1975 Fed. Rep. of Germany.
2748260 10/1977 Fed. Rep. of Germany.

Primary Examiner—Glennon H. Hollrah
Assistant Examiner—D. B. Springer
Attorney, Agent, or Firm—Jacobs & Jacobs

[57] ABSTRACT

A compound of formula (I), and salts thereof:

$$\text{(I)}$$

wherein:

$R_1$ is a $C_{1-6}$ alkoxy group;

$R_2$ and $R_3$ are the same or different and are hydrogen, halogen, $CF_3$, $C_{1-7}$ acyl, amino, $C_{1-7}$ acyl amino, aminocarbonyl or aminosulphone optionally substituted by one or two $C_{1-6}$ alkyl groups; $C_{1-6}$ alkyl-$SO_n$ wherein n is 1 or 2; or nitro;

$R_4$ is hydrogen or $C_{1-6}$ alkyl;

$R_5$ is $C_{1-6}$ alkyl or a group —$(CH_2)_s R_6$ wherein s is 1 or 2 and $R_6$ is $C_{3-8}$ cycloalkyl or phenyl, which phenyl may optionally be substituted by one or two substituents selected from $C_{1-6}$ alkyl, $C_{1-4}$ alkoxy, $CF_3$ and halogen;

n is 0 to 3;

p is 3 to 6; and r plus s is 2 to 5; may be used for the treatment of disorders of the gastro-intestinal function.

7 Claims, No Drawings

DECAHYDROQUINOLYL BENZAMIDES

This invention relates to compounds having useful pharmacological activity, to pharmaceutical compositions containing the compounds, and to a process for the preparation of the compound.

More specifically this invention relates to substituted benzamides.

West German Offenlegungsschrift No. 2748260 disclosed that compounds of the formula (A):

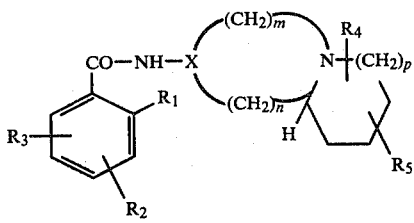

wherein:
$R_1$ is a $C_{1-6}$ alkoxy group;
$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminocarbonyl or aminosulphone optionally substituted by one or two $C_{1-6}$ alkyl groups, $C_{1-6}$ alkylsulphone or nitro groups;
X is either a nitrogen atom, in which case $m+n$ is 3 to 5, m is 2 to 4, n is 1 to 3 or X is CH in which case $m+n$ is 2 to 5, m is 1 to 5, and n is 0 to 4;
p is 0 to 3;
$R_4$ is hydrogen, $C_{1-6}$ alkyl, phenyl or phenyl-$C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; have useful pharmaceutical activity.

It has now been discovered that a class of compounds structurally distinct from the compounds of the Offenlegungsschrift have useful pharmacological activity, and in particular useful pharmaceutical activity.

Accordingly the present invention provides a compound of the formula (I), and pharmaceutically acceptable salts thereof:

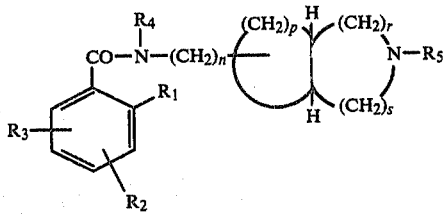

wherein:
$R_1$ is a $C_{1-6}$ alkoxy group;
$R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, $C_{1-6}$ alkoxy, hydroxy, or amino, aminocarbonyl or aminosulphonyl optionally substituted by one or two $C_{1-6}$ alkyl groups;

or $R_1$ and $R_2$ taken together are methylenedioxy or ethylenedioxy in which case $R_3$ is any one of the groups given for $R_1$ and $R_2$ above;
$R_4$ is hydrogen or $C_{1-6}$ alkyl;
$R_5$ is $C_{1-6}$ alkyl or a group $-(CH_2)_sR_6$ wherein s is 1 or 2 and $R_6$ is $C_{3-8}$ cycloalkyl or phenyl, which phenyl may optionally be substituted by one or two substituents selected from $C_{1-6}$ alkyl, $C_{1-4}$ alkoxy, $CF_3$ and halogen;
n is 0 to 3;
p is 3 to 6; and
r plus s is 2 to 5.

Suitable examples of $R_1$ include methoxy, ethoxy and n- and iso-propoxy. Preferably $R_1$ is a methoxy group.

Suitable examples of the groups $R_2$ and $R_3$ include the following atoms and groups: hydrogen, chlorine, bromine, $CF_3$, formyl, acetyl, propionyl, n- and iso-butyryl; formylamino, acetylamino, propionylamino, n- and iso-butyrylamino; methyl, ethyl and n- and iso-propylsulphone, -sulphinyl or -thia; nitro; methoxy, ethoxy and n- and iso-propoxy; hydroxy; amino, aminocarbonyl and aminosulphonyl and amino, aminocarbonyl, and aminosulphonyl substituted by one or two methyl, ethyl, n- or iso-propyl.

When $R_1$ and $R_2$ taken together are methylenedioxy or ethylenedioxy, they are most suitably ethylenedioxy.

Particularly suitable $R_2$ and $R_3$ groups include hydrogen, halogen and amino; and as "intermediates", acylamino and nitro, which can conveniently be converted to the corresponding amino groups.

It is generally preferred that $R_2$ is in the 4-position relative to the carbonyl side chain for greater activity in the resultant compound of the formula (I). For the same reason it is generally preferred that $R_3$ is in the 5-position relative to the carbonyl side chain.

Particularly preferred $R_2$ groups include 4-amino and 4-(acylated amino) as defined. Preferably $R_2$ is 4-amino. Particularly preferred $R_3$ groups include 5-halo, such as 5-chloro.

In other useful compounds $R_2$ is hydrogen, 4-halo (eg chloro), or amino; and $R_3$ is 5-$C_{1-6}$ alkyl S(O) (such as 5-methylsulphonyl, -sulphinyl or -thia) or 5-optionally alkylated aminosulphonyl.

Suitable examples of $R_4$ include hydrogen, methyl, ethyl, n- and iso-propyl, n-, sec- and tert-butyl, preferably hydrogen or methyl, in particular hydrogen.

Suitable example of $R_5$ when $C_{1-6}$ alkyl include methyl, ethyl, n- and iso-propyl and n-, sec- and tert-butyl, n-pentyl and n-hexyl.

When $R_5$ is a group $-(CH_2)_sR_6$ as defined, suitable examples of $R_6$ include $C_{5-8}$ cycloalkyl and optionally substituted phenyl as defined above. Suitable examples of such optional phenyl substitutents include methyl, ethyl, n- and iso-propyl, n, sec- and tert-butyl; methoxy, ethoxy, n- and iso-propoxy; $CF_3$, fluoro, chloro or bromo. Preferably $R_6$ when optionally substituted phenyl is unsubstituted.

Preferred examples of $R_6$ when $C_{5-8}$ cyclo-alkyl include cyclohexyl.

In the group $-(CH_2)_sR_6$, s is preferably 1.
n is suitably 0 or 1, preferably 0.
p is suitably 3 to 5, preferably 4.
r plus s is suitably 2 to 4, preferably 3. Often r is 0.

Preferably the $R_4$ substituted nitrogen atom and the $R_5$ substituted nitrogen atom are separated by three carbon atoms by the shortest route.

The salts of the compound of the formula (I) include pharmaceutically acceptable salts such as acid addition salts with conventional acids such as hydrochloric, hydrobromic, phosphoric, sulphuric, citric, tartaric, lactic and acetic acid and the like.

The salts of the compounds of the formula (I) also include quaternary ammonium salts. Examples of such salts include such compounds quaternised by compounds such as $R_7$—Y wherein $R_7$ is $C_{1-6}$ alkyl, phenyl-$C_{1-6}$ alkyl or $C_{5-7}$ cycloalkyl, and Y is an anion of an acid. Suitable examples of $R_7$ include methyl, ethyl and n- and iso-propyl; and benzyl and phenylethyl. Suitable examples of Y include the halides such as chloride, bromide and iodide.

Examples of pharmaceutically acceptable salts also include internal salts such as N-oxides.

From the aforesaid it will be seen that suitably the moiety of formula (II):

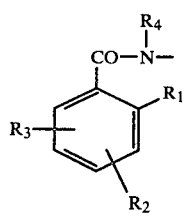

in a compound of the formula (I) will have the structure (III):

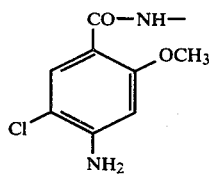

One preferred group of compounds within formula (I) is of formula (IV):

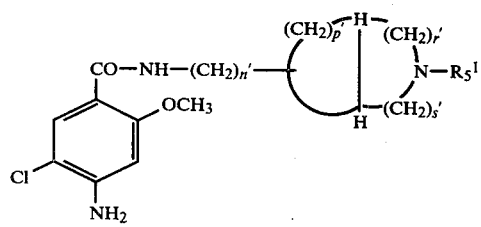

wherein:

$R_5^1$ is $C_{1-6}$ alkyl, or a group —$(CH_2)_s R_6^1$ in which s is as defined and $R_6^1$ is optionally substituted phenyl as defined;

n' is 0 or 1;
p' is 3 to 5;
r' plus s' is 2 to 4.

Suitably in formula (IV) examples of $R_5^1$ include methyl and benzyl.

Preferably in formula (IV) n' is 0.
Preferably in formula (IV) p' is 4.
Preferably in formula (IV) r' plus s' is 3. Often r' is 0.

Suitably the two side chain nitrogen atoms shown in formula (IV) are separated by three carbon atoms, by the shortest route.

Particularly suitably examples of the compounds of the present invention include those specifically prepared in the following Examples.

It will of course be realised that the compounds of the formula (I) have asymmetric centres, and thus are capable of existing in a number of stereoisomeric forms. The invention extends to each of these steroisomeric forms, and to mixtures thereof (including racemates). The different stereoisomeric forms may be separated one from the other by the usual methods, or any given isomer may be obtained by sterospecific or asymmetric synthesis.

The invention also provides a process for the preparation of a compound of the formula (I), which process comprises reacting an acid of the formula (V):

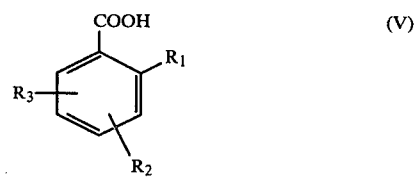

or a reactive derivative thereof, with a compound of formula (VI):

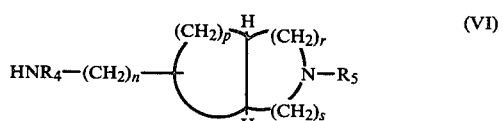

the variable groups being as defined in formula (I); and thereafter if desired or necessary converting a group $R_2$ or $R_3$ in the thus formed compound of the formula (I) to another group $R_2$ or $R_3$.

'Reactive derivative' when used herein means a derivative of the compound (V) which can be reacted with a compound (VI) to form an amido linkage between the acid group of the compound (V) and the amino group of the the compound (VI).

Often this reactive derivative will be the acid halide, such as the acid chloride or the acid (V). In such case, the reaction will normally be carried out in an inert solvent, preferably in the presence of an acid acceptor. The inert solvent can be any solvent inert to both reactants such as benzene, toluene, diethyl ether and the like. The acid acceptor is suitably an organic base such as a tertiary amine, e.g. triethylamine, trimethylamine, pyridine or picoline, or an inorganic acid acceptor, such as calcium carbonate, sodium carbonate, potassium carbonate or the like. It should also be noted that it is possible to use certain acid acceptors as the inert solvent, for example organic bases.

Another useful reactive derivative of the acid (V) that may be used is an acid ester, such as a methyl, ethyl, propyl or butyl ester, in which case the reaction is normally carried out by heating the reactants together in an inert solvent such as ethylene glycol.

The reaction may also be carried out by forming an anhydride of the acid (V) in the usual manner, and reacting that with the compound (VI); normally a conventional mixed anhydride will be used; or by reacting the acid (V) and the compound (VI) in the presence of a dehydrating catalyst such as a carbodiimide, for example dicyclohexylcarbodiimide.

The intermediates of the formulae (V) and (VI) are either known compounds or can be prepared by analogous processes to known compounds.

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_7Y$ as defined. This reaction is suitably carried out in an appropriate solvent such as acetone, methanol, ethanol, dimethylformamide and the like, at ambient or raised temperature and pressure.

The interconversion of suitable groups $R_2$ and $R_3$ after formation of a compound of the formula (I) may be carried out by conventional methods. By way of example, nitro groups may be reduced to amino groups in the normal manner, and acylamino groups may be converted to amino groups also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen. Accordingly it will be realised that compounds of the formula (I) containing an $R_2$ or $R_3$ group which is convertible to another $R_2$ or $R_3$ group are useful intermediates, and as such form an important aspect of the invention.

The compounds of the formula (I) have useful pharmaceutical activity.

In particular, compounds of the formula (I) may be used for treatment of disorders of the gastrointestinal function, such as retarded gastric emptying, dyspepsia, flatulence, oesophagal reflux or peptic ulcer. It is believed that many of the compounds of the formula (I), such as those wherein $R_5$ is $C_{1-6}$ alkyl, will combine this activity at the gastro-intestinal function with little or no CNS effects.

This invention also provides a pharmaceutical composition comprising a compound of the formula (I), or a pharmaceutically acceptable salt thereof, together with a pharmaceutically acceptable carrier. Such compositions may be adapted for oral or parental administration, and as such may be in the form of tablets, capsules, syrups, reconstitutable powders, injectable and infusable solutions or suspensions and the like; the compositions may also be in the form of suppositories and the like. Normally, orally administrable compositions are preferred.

The invention further provides a method of treatment of disorders of the gastro-intestinal function, such as retarded gastric emptying, dyspepsia, flatulence, oesophagal reflux or peptic ulcer in humans comprising the administration of a therapeutically effective amount of a compound of the formula (I) or a pharmaceutically acceptable salt thereof. The 'effective amount' will depend in the usual way on the number of factors such as the nature and severity of the malady to be treated, and the actual compound used. Usually we have found that a dose of 0.05 to 50 mg/kg per day is quite sufficient to achieve a satisfactory treatment.

Compounds of the formula (I) have the ability to potentiate the effect of conventional analgesics in migraine treatment when administered concurrently with the analgesic.

Thus the invention provides a pharmaceutical conposition comprising a compound of the formula (I) and an analgesic, together with a pharmacentucally acceptable carrier.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration or a twin pack comprising the two active ingredients made up for separate administration.

The invention accordingly provides a method of treatment of migraine in mammals including humans comprising the administration to the sufferer of a therapeutically effective amount of a compound of the formula (I) and an analgesic.

The following Examples illustrate the preparation of the compound of formula (I) and the followwing Descriptions illustrate the preparation of intermediates thereto.

It is to be noted that in formulas 1, 2, 3, 5 and 6 in these Descriptions and Examples, although the structures as drawn represent only one enantiomer, the (±) prefix is intended to show that all the compounds of formulae 1, 2, 3, 5 and 6 are infact racemic mixtures of the two possible enantiomers.

All temperatures are measured in degrees centigrade.

DESCRIPTION 1

(a) (±)-7β-Azido-1-methyl-trans-decahydroquinoline (Intermediate for Example 1 and 2)

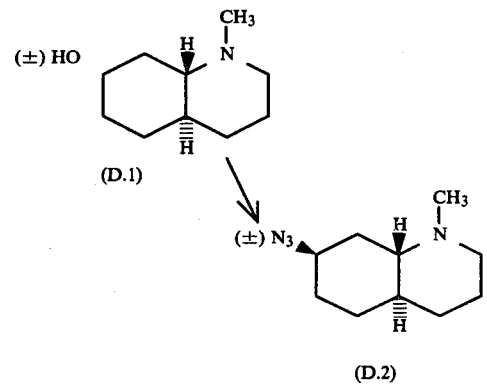

To a stirred solution of diethylazodicarboxylate (2.66 g) and triphenylphosphine (4.00 g) in dry THF (20 ml), was added dropwise, (±)-7α-hydroxy-1-methyl-trans-decahydroquinoline[1] (D.1)(2.07 g), dissolved in dry THF (10 ml), followed by diphenylphosphoryl azide (3.82 g), dissolved in dry THF (25 ml). The resulting solution was allowed to stand at room temperature for 120 hr. before the solvent was removed under reduced pressure, and the residue dissolved in chloroform (100 ml). The amines present in the resulting chloroform solution were extracted with aqueous 2N hydrochloric acid (2×50 ml) which was in turn neutralised (40% sodium hydroxide solution), saturated with potassium carbonate, and extracted with chloroform (3×75 ml). The organic phase was dried (K₂CO₃) and evaporated under reduced pressure to give a crude product which was purified by chromatography on basic alumina (50 g of grade I activity, deactivated by addition of 10% water, column diameter 4 cm), eluted with petroleum ether (40-60) to give (±)-7β-azido-1-methyl-transdecahydroquinoline (D.2) (1.85 g, 77%) as a colourless oil.

[1] C. A. Grob and H. J. Wilkens, *Helv. Chim. Acta,* 1965, 48, 808.

(b) (±)-7β-Amino-1-methyl-trans-decahydroquinoline (Intermediate for Example 1 and 2

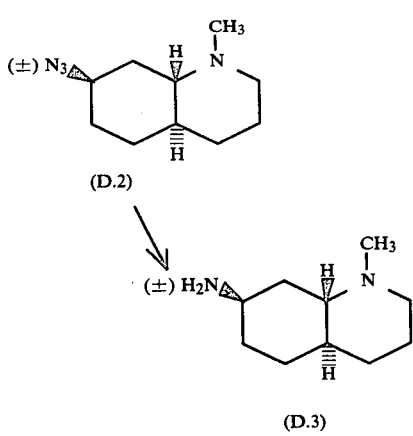

To a stirred suspension of lithium aluminium hydride (0.55 g) in dry ether (30 ml) and under an atmosphere of nitrogen, was added the azide (D.2) (1.85 g) from description 1 (a) dissolved in dry ether (30 ml), dropwise over a period of ¼ hr. Stirring was continued at room temperature for 18 hr. before water (0.5 ml), 10% aqueous sodium hydroxide (0.75 ml) and water (1.25 ml) were added sequentially. Later the solids were removed by filtration, washed well with chloroform, and the resulting solution evaporated under reduced pressure to give (±)-7β-amino-1-methyl-trans-decahydroquinoline (D.3) (1.47 g, 92%) as an oil after drying in vacuo.

DESCRIPTION 2

(a) (±)-7α-Hydroxy-1-n-butyl-trans-decahydroquinoline (D.5) (Intermediate for Example 3 and 4)

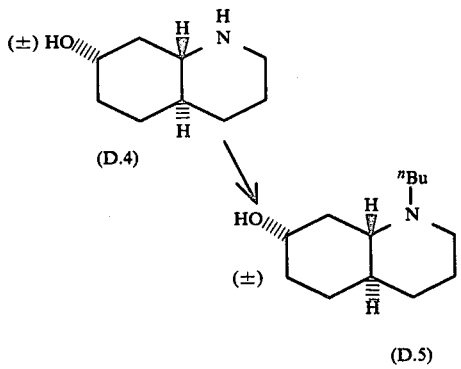

(±)-7α-hydroxy-(1H)-trans-decahydroquinoline[1] (D4) (2.3 g), dissolved in ethanol (50 ml), containing n-butanal (1.6 g), was hydrogenated over 10% Pd—C (0.4 g) under ambient conditions for four days. The catalyst was removed by filtration, and the solvent was evaporated under reduced pressure to give crude (±)-7α-hydroxy-1-n-butyl-trans-decahydroquinoline (D.5) (3.1 g, ca 99%).

[1] C. A. Grob and H. J. Wilkens, *Helv. Chim. Acta,* 1965, 48, 808.

(b) (±)-7β-Azido-1-n-butyl-trans-decahydroquinoline (D.6) (Intermediate for Example 2)

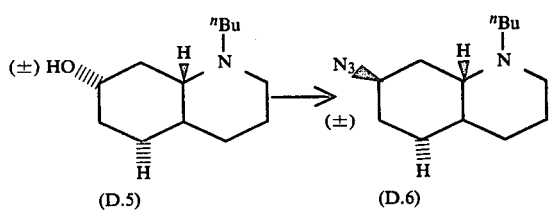

Following the procedure outlined in Description 1(a) (±)-7α-hydroxy-n-butyl-trans-decahydroquinoline (D.5) (3.1 g) was converted to (±)-7β-azido-1-n-butyl-trans-decahydroquinoline (D.6) (2.14 g, 61%).

i.r. (film) $v_{(N3)}$: 2 100 cm$^{-1}$.

(c) (±)-7β-Amino-1-n-butyl-trans-decahydroquinoline (D.7) (Intermediate for Example 3 and 4)

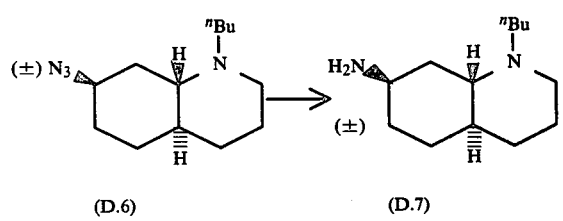

Following the procedure outlined in Description 1(b), (±)-7β-azido-1-n-butyl-trans-decahydroquinoline (D.6) (2.14 g), was converted to (±)-7β-amino-1-n-butyl-trans-decahydroquinoline (D.7) (2.05, ca 100%).

DESCRIPTION 3

(a) (±)-7β-Azido-1-benzyl-trans-decahydroquinoline (D.9) (Intermediate for Example 5 and 6)

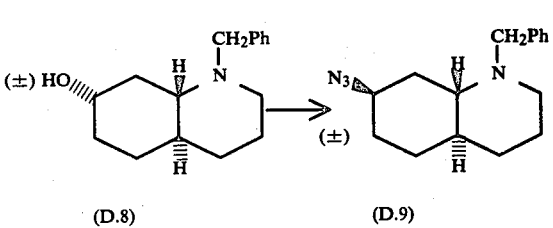

Following the procedure outlined in Description 1(a) (±)-7α-hydroxy-1-benzyl-trans-decahydroquinoline (D.8)[2] (2.58 g) was converted to (±)-7β-azido-1-benzyl-trans-decahydroquinoline (D.9) (1.42 g, 50%).

[2] R. A. Johnson, H. C. Murray, L. M. Reineke, and G. S. Fanken, *J. Org. Chem.,* 1968, 33, 3207 i.r. (film) $v_{(N3)}$: 2 100 cm$^{-1}$.

(b) (±)-7β-Amino-1-benzyl-trans-decahydroquinoline (D.10) (Intermediate for Example 5 and 6)

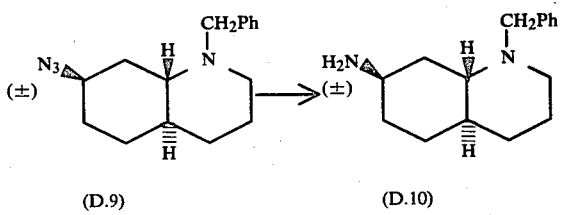

Following the procedure outlined in Description 1(b), (±)-7β-azido-1-benzyl-trans-decahydroquinoline (D.9) (1.42 g), was converted to (±)-7β-amino-1-benzyl-trans-decahydroquinoline (D.10) (1.44 g, ca 100%).

DESCRIPTION 4

(a) (±)-1-Benzyl-trans-decahydro-7-quinolinone (D.11) (Intermediate for Example 7 and 8)

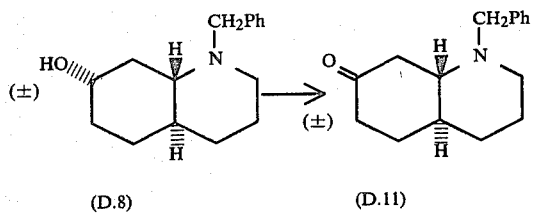

To (±)-7α-hydroxy-1-benzyl-trans-decahydroquinoline (D.8) (2.5 g), dissolved in 7N aqueous sulphuric acid (10 ml), at 0°, was added chromium trioxide (0.88 g), dissolved in 7N aqueous sulphuric acid (10 ml), over a period of ca. 5 minutes, with stirring. After 2 h at room temperature, the solution was made basic with 20% aqueous sodium hydroxide solution, and the aqueous phase was extracted with chloroform (3×100 ml). The combined organic extracts were dried (K₂CO₃) and evaporated under reduced pressure, and the crude product was purified by chromatography (silica gel, ether) to give (±)-1-benzyl-trans-decahydro-7-quinolinone (D.11) (1.17 g, 56%, Rf (ether) 0.64) as an oil.

i.r. (film) $\nu_{(C=O)}$: 1705 cm⁻¹.

n.m.r. (δCDCl₃): 0.90–3.10 (14H, m, methylene plus methine protons); 3.52 (2H, ABq, 14 Hz, 40 Hz, —N—CH₂Ph); 7.25 (5H, s, aromatic protons).

(b) (±)-1-Benzyl-trans-decahydro-7-quinolinone oxime (D.12) (Intermediate for Example 7 and 8)

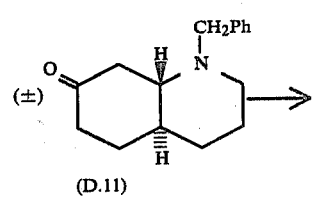

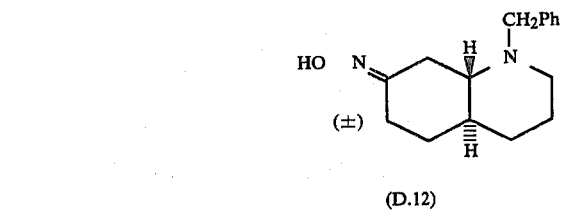

To (±)-1-benzyl-trans-decahydro-7-quinolinone (D.11) (1.17 g), dissolved in ethanol (20 ml) and pyridine (0.8 ml), was added hydroxylamine hydrochloride (0.4 g), and the mixture was heated under reflux for 1 hr. On cooling, the ethanol was removed under reduced pressure and the residue was treated with dilute potassium carbonate solution. The product was extracted with chloroform and dried (K₂CO₃). Removal of the solvent afforded crude (±)-1-benzyl-trans-decahydro-7-quinolinone oxime (D.12) (1.1. g, ca 88%).

(c) (±)-7α-Amino-1-benzyl-trans-decahydroquinoline (D.13) (Intermediate for Example 7 and 8)

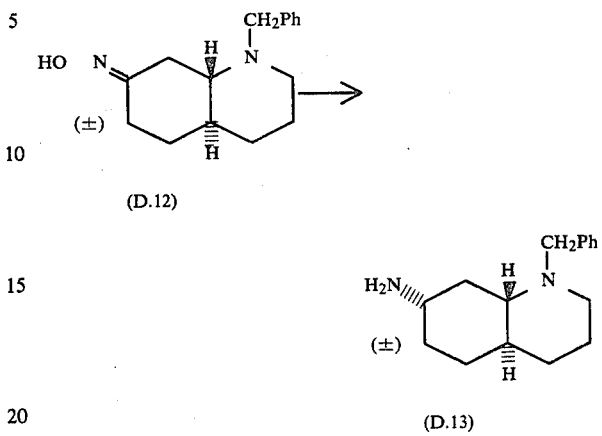

To the crude (±)-1-benzyl-trans-decahydro-7-quinolinone oxime D.12) (1.1 g), dissolved in amyl alcohol (30 ml), and heated under reflux, was added sodium metal (4.0 g) portionwise over 1 hr. The cooled reaction mixture was then treated with 5N hydrochloric acid (ca 30 ml) and extracted with ethyl acetate. The acidic aqueous layer was separated, neutralised and saturated with potassium carbonate and re-extracted with methylene chloride (4×80 ml). The combined halogenated organic extracts were dried (K₂CO₃), and evaporated under reduced pressure to give crude (±)-7α-amino-1-benzyl-trans-decahydroquinoline (D.13) (1.0 g, ca 96%).

DESCRIPTION 5

(a) (±)-1-Methyl-trans-decahydro-8-quinolinone (D.15) (Intermediate for Example 9 and 10)

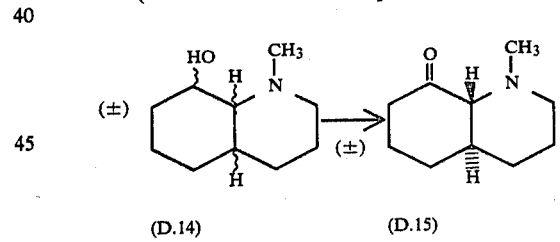

To (±)-8-hydroxy-1-methyl decahydroquinoline (D.14)³ (24.3 g), dissolved in 7M aqueous sulphuric acid (140 ml), at 0°, was added chromium trioxide (15.2 g), dissolved in 7M aqueous sulphuric acid (270 ml) over a period of ½ h, with stirring. After stirring for an additional 1 hr at room temperature, the solution was made basic with 40% sodium hydroxide solution, and the aqueous phase was extracted with chloroform (3×600 ml). The combined organic extracts were dried (K₂CO₃) and evaporated under reduced pressure. The resulting cis, trans-quinolinone was dissolved in absolute methanol (200 ml) and treated with sodium methoxide (ca 0.8 g). After 72 hr at room temperature, the solvent was removed under reduced pressure and the product was partitioned between chloroform and saturated aqueous potassium carbonate. Distillation of the organic extracts gave (±)-1-methyl-trans-decahydro-8-quinolinone (D.15) (8.69, 36%). (This product contained a small quantity (<20%) of the corresponding cis isomer).

[3] I. Jézo, M. Karvas and R. T. Llarik, Chem. zvesti, 1960, 14, 182–6; Chem. Abs., 1960, 54, 21092a.

b.p.: 88°–90°/1 mm Hg.

(b) (±)-8α-Cyano-1-methyl-trans-decahydroquinoline (D.16) (Intermediate for Example 9 and 10)

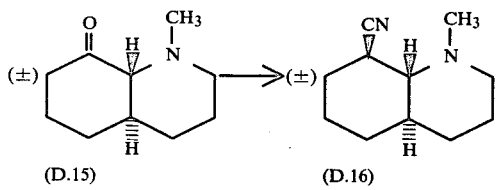

To tosyl-methyl isocyanide (10.75 g), dissolved in dry dimethyl sulphoxide (55 ml), and cooled to 0°, was added solid potassium tert butoxide (18.2 g) portionwise. The whole was stirred for ca 5 minutes, before (±)-1-methyl-trans-decahydro-8-quinolinone (D.15) (6.20 g) and absolute methanol (2.7 ml) were added in one portion. After stirring for an additional 24 h at room temperature, the whole was added to water (300 ml), and the pH was adjusted to ca 4-5, with dilute hydrochloric acid. Extraction of the aqueous phase with ether gave, after purification by chromatography (silica gel, ethyl acetate), (±)-8α-cyano-1-methyl-trans-decahydroquinoline (D.16) (3.05, 46%) as low melting solid, mp. 53°–54°.

i.r. (film) ν(CN): 2 225 cm⁻¹.

(c) (±)-8α-Aminomethyl-1-methyl-trans-decahydroquinoline (D.17) (Intermediate for Example 9 and 10)

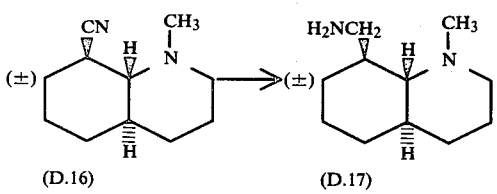

Following the procedure outlined in Description 1(b), (±)-8α-cyano-1-methyl-trans-decahydroquinoline (D.16) (4.18 g) was converted to (±)-8α-aminomethyl-1-methyl-trans-decahydroquinoline (D.17) (4.24 g, ca 100%).

i.r. (film) ν(NH2): 3 300 (br) cm⁻³.

DESCRIPTION 6

(a) (±)-1-Methyl-trans-decahydro-5-quinolinone oxime (D.19) (Intermediate for Example 11, 12, 13 and 14)

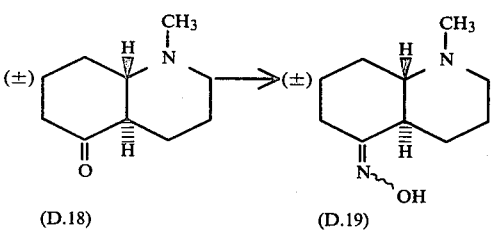

Following the procedure described in Description 4(b), (±)-1methyl-trans-decahydro-5-quinolinone[4] (D.18) (3.59 g) was converted to (±)-1-methyl-trans-decahydro-5-quinolinone oxime (D.19) (2.86 g, 75%), m.p. 169°–171°.

[4] C. A. Grob and H. R. Kiefer, Helv. Chim. Acta, 1965, 48 799–808.

(b) (±)-5α,β-Amino-1-methyl-trans-decahydroquinoline (D.20) (Intermediate for Example 11, 12, 13 and 14)

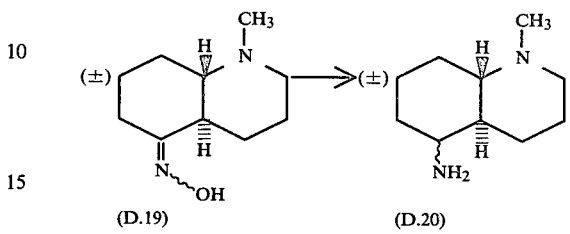

To a stirred suspension of lithium aluminium hydride (0.55 g) in dry tetrahydrofuran (30 ml) and under an atmosphere of nitrogen, was added (±)-1-methyl-trans-decahydro-5-quinolinone oxime (D.19) (2.86 g), dissolved in dry tetrahydrofuran (80 ml), dropwise over a period of ¼ hr. The whole was heated under reflux, with stirring, for 18 hr. before being allowed to cool to room temperature and water (0.5 ml), 10% aqueous sodium hydroxide (0.75 ml) and water (1.25 ml) were added sequentially. Later the solids were removed by filtration and washed well with methylene chloride, and the resulting solution was evaporated under reduced pressure to give (±)-5α,β-amino-1-methyl-trans-decahydroquinoline (D.20) (2.62 g, ca 100%) as an oil.

EXAMPLE 1

4-Acetamido-5-chloro-2-methoxy-N-[(±)-7β-(1-methyl-trans-decahydroquinolyl)]-benzamide (1)

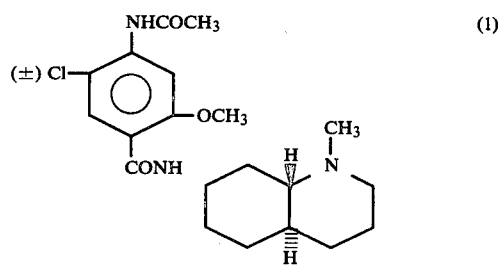

To 4-acetamido-5-chloro-2-methoxybenzoyl chloride (2.75 g), dissolved in toluene (ca 200 ml) and triethylamine (5 ml) was added crude (±)-7β-amino-1-methyl-trans-decahydroquinoline (D.3) (1.47 g), dissolved in toluene (50 ml). The reaction mixture was stirred at room temperature for 2.5 hr., then treated with 2.5N sodium hydroxide (20 ml). The toluene layer was separated, the aqueous layer was extracted with methylene chloride (3×100 ml), and the combined organic extracts were dried (K₂CO₃). The solvent was removed and chromatography of the product (basic alumina, Brockman III, methylene chloride) gave 4-acetamido-5-chloro-2-methoxy-N-[(±)-7β-(1-methyl-trans-decahydroquinolyl)]benzamide (1) (2.5 g, 73%).

n.m.r. (δ, CDCl₃): 0.90–2.40 (12H, m, methylene protons plus methine ring junction protons); 2.20 (3H, s, —N—CH₃); 2.30 (3H, s, —NHCOCH₃); 2.60–3.10 (2H, m, methylene protons α-to nitorgen); 4.00 (3H, s, —OCH₃); 4.25–4.70 (1H, m, —CONH—CH—, equatorial); 7.66–7.95 (1H, m, —NHCOCH₃); 8.10–8.40 (1H, m, —CONH—); 8.15 (1H, s, aromatic proton); 8.30 (1H, s, aromatic proton).

EXAMPLE 2

4-Amino-5-chloro-2-methoxy-N-[(±)-7β-(1-methyl-trans-decahydroquinolyl)]-benzamide (2)

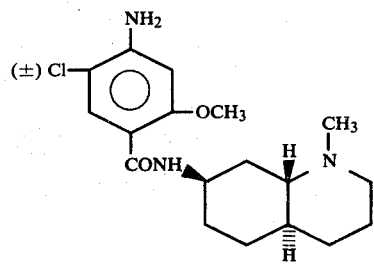

To 4-Acetamido-5-chloro-2-methoxy-N-[(±)-7β-(1-methyl-trans-decahydroquinolyl)]-benzamide (1) (2.5 g), dissolved in ethanol (50 ml) was added 10% aqueous sodium hydroxide solution (10 ml), and the whole was heated under reflux for 2 hr. The mixture was cooled to room temperature, the solvent was removed under reduced pressure, and the residue was treated with chloroform (50 ml), water (5 ml) and saturated aqueous potassium carbonate (30 ml). The aqueous phase was further extracted with chloroform (3×50 ml) and the combined organic extracts were dried ($K_2CO_3$). The solvent was removed under reduced pressure to give a solid which was chromatographed (basic alumina, Brockmann III, methylene chloride, chloroform) and recrystallised (ethyl acetate) to give 4-amino-5-chloro-2-methoxy-N-[(±)-7β-(1-methyl-trans-decahydroquinolyl)]-benzamide (2) (1.17 g, 52%), mp. 205°–206°.

n.m.r. (δ, CDCl3): 0.09–2.00 (11H, m, methylene protons plus one methine ring junction proton); 2.15 (4H, s plus m, N—CH3 plus methine proton α- to nitrogen); 2.65–3.05 (2H, m, methylene protons α- to nitrogen); 3.95 (3H, s, —OCH3); 4.15–4.65 (1H, m, —CONH—CH—, equatorial); 5.45 (2H, brs, —NH2); 6.52 (1H, s, aromatic proton); 7.90 (2H, s, aromatic proton plus —CONH—).

EXAMPLE 3

4-Acetamido-5-chloro-2-methoxy-N-[(±)-7β-(1-n-butyl-trans-decahydroquinolyl)]-benzamide (3)

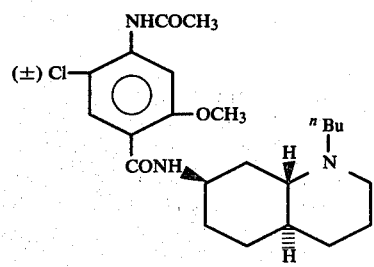

Following the procedure outlined in Example 1, (±)-7β-amino-1-n-butyl-trans-decahydroquinoline (D.7) (2.14 g) was converted to 4-acetamido-5-chloro-2-methoxy-N-[(±)-7β-(1n-butyl-trans-decahydroquinolyl)]-benzamide (3) (3.36 g, 76%) as a foam.

EXAMPLE 4

4-Amino-5-chloro-2-methoxy-N-[(±)-7β-(1-n-butyl-trans-decahydroquinolyl)]-benzamide (4)

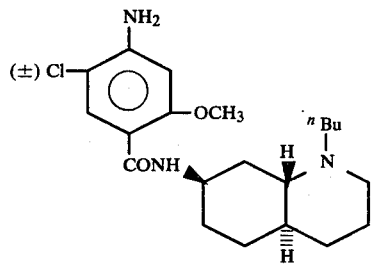

Following the procedure outlined in Example 2, 4-Acetamido-5-chloro-2-methoxy-N-[(±)-7β-(1-n-butyl-trans-decahydroquinolyl)]-benzamide (3) (3.36 g) was converted to 4-amino-5-chloro-2-methoxy-N-[(±)-7β-(1-n-butyl-trans-decahydroquinolyl)]-benzamide (4) (2.53 g, 84%). mp. 156°–157°.

n.m.r. (δCDCl3): 0.80–3.10 (21H, m, methylene plus ring junction methine protons); 3.91 (3H, s, —OCH3); 4.30–4.70 (1H, m, —CONH—CH—, equatorial); 4.70 (2H, br. s, —NH2); 6.39 (1H, s, aromatic proton); 7.80–8.10 (1H, m, —CONH—); 8.05 (1H, s, aromatic proton).

EXAMPLE 5

4-Acetamido-5-chloro-2-methoxy-N-[(±)-7β-(1-benzyl-trans-decahydroquinolyl)]-benzamide (5)

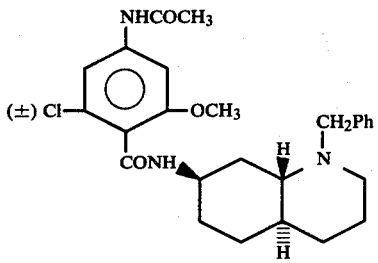

Following the procedure outlined in Example 1, (±)-7β-amino-1-benzyl-trans-decahydroquinoline (D.10) (1.44 g) was converted to crude 4-acetamido-5-chloro-2-methoxy-N-[(±)-7β-(1-benzyl-trans-decahydroquinolyl)]-benzamide (5) (2.8 g) which was used without purification.

EXAMPLE 6

4-Amino-5-chloro-2-methoxy-N-[(±)-7β-(1-benzyl-trans-decahydroquinolyl)]-benzamide (6)

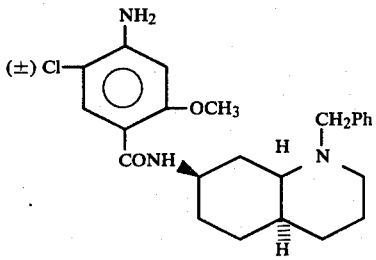

Following the procedure outlined in Example 2, 4-acetamido-5-chloro-2-methoxy-N-[(±)-7β-(1-benzyl-trans-decahydroquinolyl)]-benzamide (5) (2.8 g) was converted to the crude benzamide (6) (2.1 g), which was found to contain some of the equatorial isomer (8). Purification by chromatography (silica gel, 70% ethyl acetate:30% chloroform (v/v)) gave the equatorial isomer (8) (0.5 g, Rf (EtOAc) 0.3) and 4-amino-5-chloro-2-methoxy-N-[(±)-7β-(1-benzyl-trans-decahydroquinolyl)]-benzamide (1.0 g, 40%, Rf (EtOAc) 0.2), as a foam.

n.m.r. (δCDCl₃): 0.50–2.20 (11H, m, methylene protons plus one methine ring junction proton); 2.20–3.10 (3H, m, methylene protons α- to nitrogen plus one methine ring junction proton); 3.10–3.90 (2H, m, —NCH₂Ph); 3.72 (3H, s, —OCH₃); 4.10–4.80 (3H, m, —NH₂ plus —CONH—CH-equatorial); 6.25 (1H, s, aromatic proton); 7.05 (5H, s, —NCH₂C₆H₅); 7.80–8.10 (1H, m, —CONH—); 8.05 (1H, s, aromatic proton).

EXAMPLE 7

4-Acetamido-5-chloro-2-methoxy-N-[(±)-7β-(1-benzyl-trans-decahydroquinolyl)]-benzamide (7)

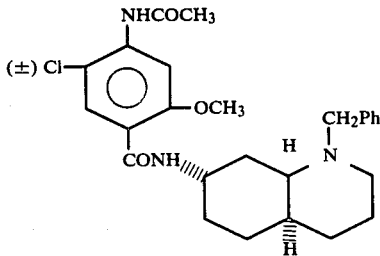
(7)

Following the procedure outlined in Example 1, (±)-7α-amino-1-benzyl-trans-decahydroquinoline (D.13) (1.0 g) was converted to crude 4-acetamido-5-chloro-2-methoxy-N-[(±)-7β-(1-benzyl-trans-decahydroquinolyl)]-benzamide (7) (1.85 g) which was used without purification.

EXAMPLE 8

4-Amino-5-chloro-2-methoxy-N-[(±)-7α-(1-benzyl-trans-decahydroquinolyl)]-benzamide (8)

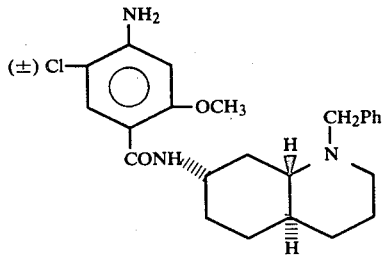
(8)

Following the procedure outlined in Example 2, 4-acetamido-5-chloro-2-methoxy-N-[(±)-7α-(1-benzyl-trans-decahydroquinolyl)]-benzamide (7) (1.85 g) was converted to crude benzamide (8). Purification by chromatography (silica gel, 50% ethyl acetate:chloroform (v/v)) and recrystallisation (EtOAc) gave 4-amino-5-chloro-2-methoxy-N-[(±)-7α-(1-benzyl-trans-decahydroquinolyl)]-benzamide (8) (0.6 g, 36%), mp. 235°–236° dec.

n.m.r. (δ, CDCl₃): 0.40–2.50 (12H, m, methylene protons plus methine ring junction protons); 2.30–2.95 (2H, m, methylene proton α- to nitrogen); 2.95–3.65 (2H, m, —N—CH₂Ph); 3.80–4.10 (1H, m, —CONH—CH—, axial); 3.86 (3H, s, —OCH₃); 4.97 (2H, br. s, —NH₂); 6.41 (1H, s, aromatic proton); 7.27 (5H, s, —NCH₂—NCH₂—C₆H₅); 7.50–7.80 (1H, m, —CONH—); 7.99 (1H, s, aromatic proton).

EXAMPLE 9

4-Acetamido-5-chloro-2-methoxy-N[(±)-8α-(1-methyl-trans-decahydroquinolylmethyl)]-benzamide (9)

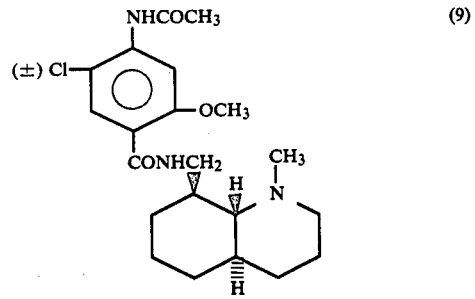
(9)

Following the procedure outlined in Example 1, (±)-8α-aminomethyl-1-methyl-trans-decahydroquinoline (D.17) (4.24 g) was converted to crude 4-acetamido-5-chloro-2-methoxy-N-[(±)-8β-(1-methyl-decahydroquinolylmethyl)]-benzamide (9) (6.00 g, ca 65%).

n.m.r. (δ, CDCl₃): 0.60–2.30 (13H, m, methyleen protons plus methine protons; 2.25 (6H, s, —NHCOCH₃ plus —N—CH₃); 2.60–3.20 (2H, m, methylene protons α- to nitrogen); 3.70–4.20 (2H, m, CONH—CH₂—); 3.95 (3H, s, —OCH₃); 7.70–8.40 (2H, m, —NHCOCH₃ plus —CONH—); 8.15 (1H, s, aromatic proton); 8.22 (1H, s, aromatic proton).

EXAMPLE 10

4-Amino-5-chloro-2-methoxy-N-[(±)-8α-(1-methyl-trans-decahydroquinolylmethyl)]-benzamide (10)

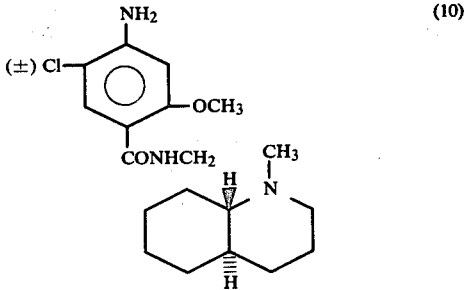
(10)

Following the procedure outlined in Example 2, 4-acetamido-5-chloro-2-methoxy-N-[(±)-8α-(1-methyl-trans-decahydroquinolylmethyl)]-benzamide (9) (6.00 g) was converted to 4-amino-5-chloro-2-methoxy-N-[(±)-8β-(1-methyl-trans-decahydroquinolylmethyl)]-benzamide (10) (2.48 g, 45%), mp. 190°–191°.

n.m.r. (δ, CDCl₃): 0.60–2.00 (12H, m, methylene protons plus two methine protons); 2.00–2.50 (2H, m, methylene protons α- to nitrogen); 2.25 (3H, s, —N—CH₃); 2.50–3.10 (1H, m, methine proton α- to nitrogen); 3.40–4.00 (2H, m, —CONHCH₂—); 3.85 (3H, s, —OCH₃); 4.63 (2H, br. s, —NH₂, exchangable with D₂O); 6.30 (1H, s, aromatic proton); 7.80–8.20 (1H, m, —CONH—); 8.05 (1H, s, aromatic proton).

EXAMPLES 11 AND 12

4-Acetamido-5-chloro-2-methoxy-N-[(±)-5α-(1-methyl-trans-decahydroquinolyl)]-benzamide (11)
4-Acetamido-5-chloro-2-methoxy-N-[(±)-5β-(1-methyl-trans-decahydroquinolyl)]-benzamide (12)

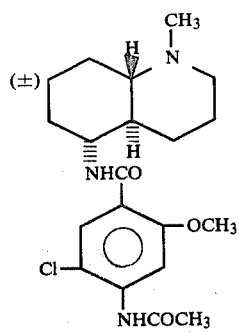

(11)

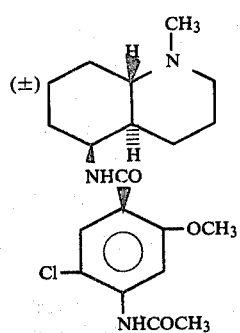

(12)

Following the procedure outlined in Example 1, (±)-5α,β-amino-1-methyl-trans-decahydroquinoline (D.20), (2.62 g) was converted to a mixture of the crude benzamides (11) and (12) (6.00 g). Treatment of this product with ether (30 ml) gave 4-acetamido-5-chloro-2-methoxy-N-[(±)-5α-(1-methyl-trans-decahydroquinolyl)]-benzamide (11) (1.75 g, 29%), mp. 188°–190° dec., as a white solid after collection by filtration and drying in vacuo. Evaporation of the residual organic solution under reduced pressure, gave 4-acetamido-5-chloro-2-methoxy-N-[(±)-5β-(1-methyl-trans-decahydroquinolyl)]-benzamide (12) (2.71 g, ca 44%) as a foam, which contained a small quantity of the benzamide (11).

n.m.r. (11) (δ, CDCl₃): 0.80–2.40 (12H, m, methylene protons plus methine ring junction protons); 2.15 (6H, s, —NHCOCH₃ plus —NCH₃); 2.50–3.10 (2H, m, methylene protons α- to nitrogen); 3.90 (3H, s, —OCH₃); 3.90–4.10 (1H, m, —CONH—CH—, axial); 7.10–8.30 (2H, m, —CONH— plus —NHCOCH₃); 8.00 (1H, s, aromatic proton); 8.12 (1H, s, aromatic proton).

n.m.r. (12) (δ, CDCl₃): 0.70–2.40 (12H, m, methylene protons plus methine ring junction protons); 2.20 (6H, m, —NHCOCH₃ plus —NCH₃); 2.50–3.10 (2H, m, methylene protons α- to nitrogen); 3.90 (3H, s, —OCH₃); equatorial); 7.60–8.35 (2H, m, —CONH— plus —NHCOCH₃); 8.10 (1H, s, aromatic proton); 8.25 (1H, s, aromatic proton).

EXAMPLE 13

4-Amino-5-chloro-2-methoxy-N-[(±)-5α-(1-methyl-trans-decahydroquinolyl)]-benzamide (13)

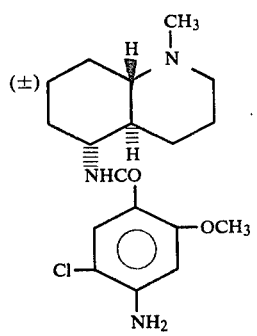

(13)

Following the procedure outlined in Example 2, 4-acetamido-5-chloro-2-methoxy-N-[(±)-5α-(1-methyl-trans-decahydroquinolyl)]-benzamide (11) (1.75 g) was converted to 4-amino-5-chloro-2-methyl-N-[(±)-5α-(1-methyl-trans-decahydroquinolyl)]-benzamide (13) (1.37 g, 87%) as a foam after purification by chromatography (basic alumina, Brockman II, methylene chloride).

n.m.r. (δ, CDCl₃): 0.60–2.45 (12H, m, methylene protons plus methine ring junction protons); 2.28 (3H, s, —NCH₃); 3.60–4.25 (m, 1H, —CONH—CH—, axial); 3.86 (3H, s, —OCH₃); 6.30 (1H, s, aromatic proton); 7.20–7.60 (1H, m, —CONH—); 8.07 (1H, s, aromatic proton).

4-Amino-5-chloro-2-methoxy-N-[(±)-5α-(1-methyl-trans-decahydroquinolyl)]-benzamide (13) was also obtained if (±)-1-methyl-cis-decahydro-5-quinolinone was used in place of the trans isomer (D.18) in descriptions 6(a) and 6(b), and Examples 11, 12 and 13.

EXAMPLE 14

4-Amino-5-chloro-2-methoxy-N-[(±)-5β-1-methyl-trans-decahydroquinolyl]-benzamide (14)

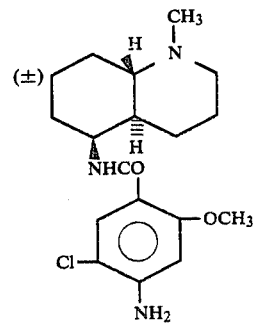

(14)

Following the procedure outlined in Example 2, 4-acetamido-5-chloro-2-methoxy-N-[(±)-5β-(1-methyl-trans-decahydroquinolyl)]-benzamide (12) (2.71 g) was converted to 4-amino-5-chloro-2-methoxy-N-[(±)-5β-(1-methyl-trans-decahydroquinolyl)]-benzamide (14) (1.45 g, 60%, mp. 223°–224°.

n.m.r. (δ, CDCl₃): 0.80–2.30 (12H, m, methylene protons plus methine ring junction protons); 2.28 (3H, s, —NCH₃); 2.60–3.20 (1H, m, methylene protons α- to nitrogen); 3.95 (3H, s, —OCH₃); 4.22–4.55 (3H, m, —NHCO—CH— equatorial plus —NH₂); 6.33 (1H, s, aromatic proton); 7.80–8.10 (1H, m, —CON$\underline{H}$—); 8.10 (1H, s, aromatic proton).

4-Amino-5-chloro-2-methoxy-N-[(±)-5β-(1-methyl-trans-decahydroquinolyl)]-benzamide (14) was also obtained if (±)-1-methyl-cis-decahydro-5-quinolinone was used in place of the trans isomer (D.18) in descriptions 6(a) and 6(b) and Examples 11, 12 and 14.

Pharmacological Data Section

Compound 2 was tested for the following activities:
(a) Increase in intragastric pressure Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after administration of compound. Student's "t" test was applied to the difference in average values obtained for spontaneous and post compound activity.

Compound 2 significantly increased the index of activity post administration at dose levels of 0.5 mg/kg subcutaneously and 1.0 mg/kg intragastrically.

(b) Inhibition of stereotype behaviour induced by apomorphine in the rat

This is indicative of dopamine receptor blockade in the central nervous system.

The method of Ernst A. M. (1967) Psychopharmacologia (Berl.), 10, pp. 316–323 was followed.

No inhibition of apomorphine induced stereotype was observed at a dose level of 50 mg/kg subcutaneously and Compound 2 is therefore devoid of central dopamine receptor blocking activity.

Toxicity

No signs of toxicity were observed at any of the dose levels of Compound 2 tested.

I claim:

1. A compound of the formula (I) or a pharmaceutically acceptable salt thereof:

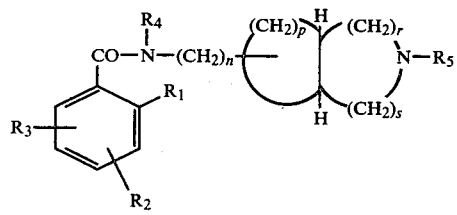

wherein:
$R_1$ is a $C_{1-6}$ alkoxy group;
$R_2$ and $R_3$ are the same or different and are hydrogen, halogen, $CF_3$, $C_{1-7}$ alkanoyl, $C_{1-7}$ alkanoylamino, wherein n is 0, nitro, $C_{1-6}$ alkoxy, hydroxy, amino or aminocarbonyl optionally substituted by one or two $C_{1-6}$ alkyl groups;
or $R_1$ and $R_2$ taken together are methylenedioxy or ethylenedioxy in which case $R_3$ is any one of the groups given for $R_1$ and $R_2$ above;
$R_4$ is hydrogen or $C_{1-6}$ alkyl;
$R_5$ is $C_{1-6}$ alkyl;
p is 4,
r is 0, and
s is 3.

2. A compound according to claim 1 of formula (IV):

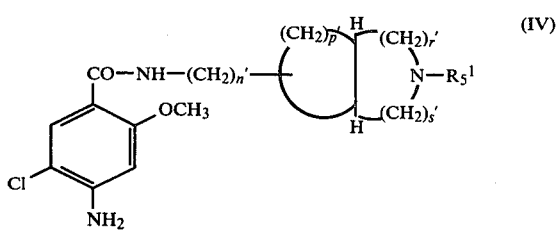

wherein:
$R_5^1$ is $C_{1-6}$ alkyl, or a group —$(CH_2)_sR_6^1$ in which s is 3 and $R_6^1$ is optionally substituted phenyl as defined in claim 1;
n' is 0;
p' is 4;
r' is 0 and s' is 3.

3. A compound according to claim 2 which is:
4-Acetamido-5-chloro-2-methoxy-N-[(±)-7β-(1-methyl-trans-decahydroquinolyl)]-benzamide, or
4-Amino-5-chloro-2-methoxy-N-[(±)-7α-(1-methyl-trans-decahydroquinolyl)]-benzamide
or a pharmaceutically acceptable salt thereof.

4. A compound according to claim 3 which is 4-acetamido-5-chloro-2-methoxy-N-[(±)-7β(1-methyl-trans-decahydroquinolyl)]-benzamide.

5. A compound according to claim 1 which is 4-acetamido-5-chloro-2-methoxy-N-[(±)-8α-(1-methyl-trans-decahydroquinolylmethyl)]-benzamide, 4-amino-5-chloro-2-methoxy-N-[(±)-8α-(1-methyl-trans-decahydroquinolylmethyl)]-benzamide, or a pharmaceutically acceptable salt thereof.

6. A compound according to claim 1 which is the isomer of 4-acetamido-5-chloro-2-methoxy-N-[(±)-8-(1-methyl-trans-decahydroquinolyl)]-benzamide having the $^1H$ nmr spectrum:
δ: 0.60–2.30 (13H, m), 2.25 (6H, s) 2.60–3.20 (2H, m), 370–4.20 (2H, m), 3.95 3H, s), 7.70–8.40 (2H, m), 8.15 (1H, s), 8.22 (1H, s),
or a pharmaceutically acceptable salt thereof.

7. A compound according to claim 1 which is the isomer of 4-amino-5-chloro-2-methoxy-N-[(±)-8-(1-methyl-trans-decahhydroquinolyl)]-benzamide having the $^1H$ nmr spectrum:
δ: 0.60–2.30 (12H, m), 2.25 (3H, s), 2.50–3.10 (1H, m) 3.40–4.00 (2H, m), 3.85 (3H, s), 4.63 (2H, brs) 6.30 (1H, s), 7.80–8.20 (1H, m), 8.05 (1H, s)
and a melting point of 190°–191° C.,
or a pharmaceutically acceptable salt thereof.

* * * * *